US006407082B1

(12) United States Patent
Rodriguez et al.

(10) Patent No.: US 6,407,082 B1
(45) Date of Patent: Jun. 18, 2002

(54) PREVENTION OF OVARIAN CANCER BY ADMINISTRATION OF A VITAMIN D COMPOUND

(75) Inventors: Gustavo C. Rodriguez, Durham; Regina Salas Whitaker, Hillsborough, both of NC (US)

(73) Assignee: New Life Pharmaceuticals Inc., Chicago, IL (US)

( * ) Notice: Subject to any disclaimer, the term of this patent is extended or adjusted under 35 U.S.C. 154(b) by 0 days.

(21) Appl. No.: 09/479,837

(22) Filed: Jan. 7, 2000

Related U.S. Application Data

(63) Continuation of application No. 08/873,010, filed on Jun. 11, 1997, now Pat. No. 6,034,074, which is a continuation-in-part of application No. 08/713,834, filed on Sep. 13, 1996, now Pat. No. 6,028,064.

(51) Int. Cl.$^7$ .......................... A61K 31/59; A61K 31/56
(52) U.S. Cl. ........................................ 514/167; 514/171
(58) Field of Search .................................. 514/167, 171

(56) References Cited

U.S. PATENT DOCUMENTS

| 6,310,054 B1 | 10/2001 | Rodriguez .................. 514/179 |
| 6,319,911 B1 | 11/2001 | Rodriguez .................. 514/170 |

OTHER PUBLICATIONS

Grimes et al., "Primary Prevention Of Gynecologic Cancers," *Am. J. Obstetrics And Gynecology,* 172(1):227–235 (1995).

Rosenberg et al., (The WHO Collaborative Study of Neoplasia and Steroid Contraceptives) "A Case Control DStudy Of Oral Contraceptive Use And Invasive Epithelial Overian Cancer," *Am. J. Epidem,* 139:654–661 (1994).

Pfleiderer, di Problematik einer prophylaktischen Chemotherapie, einer der Remission bei der Therapie des Ovarialkarzinoms, *Gerburstsh u. Frauenheilk,* 36(2):132–139 (1976).

English translation of A. Pfleiderer: The Problems Of Prophylactic Chemotherapy, Second–Look Surgery, And Maintenance Of Remission In Therapy Of Ovarian Cancer, Geburtshilfe und Frauenheilkunde, vol. 36 (1976), pp. 132–139.

U.S. patent application Ser. No. 09/479,021 filed on Jan. 7, 2000 (Inventor: Rodriguez et al); Notice of Allowance mailed on Jun. 22, 2001; Issue Fee paid by attorney for applicant on Jun. 6, 2001.

*Primary Examiner*—Jerome D. Goldberg
(74) *Attorney, Agent, or Firm*—Raymond N. Nimrod

(57) ABSTRACT

The present invention relates to methods for preventing the development of epithelial ovarian cancer by administering a Vitamin D compound in an amount capable of increasing apoptosis in non-neoplastic ovarian epithelial cells of the female subject.

12 Claims, No Drawings

PREVENTION OF OVARIAN CANCER BY ADMINISTRATION OF A VITAMIN D COMPOUND

This application is a continuation of co-pending application Ser. No. 08/873,010, filed on Jun. 11, 1997 and issued as U.S. Pat. No. 6,034,074 on Mar. 7, 2000, which is a continuation-in-part of U.S. Ser. No. 08/713,834, filed Sep. 13, 1996 and issued as U.S. Pat. No. 6,028,064 on Feb. 22, 2000. The present invention relates generally to methods of preventing the development of ovarian cancer by administering Vitamin D compounds including Vitamin D, and biologically active analogues and derivatives thereof.

FIELD OF THE INVENTION

Background of the Invention

Ovarian cancer is the fourth leading cause of cancer deaths among women in the United States and causes more deaths than all other gynecologic malignancies combined. In the United States, a woman's lifetime risk of developing ovarian cancer is 1 in 70. In 1992, about 21,000 cases of ovarian cancer were reported, and about 13,000 women died from the disease. Chapter 321, *Ovarian Cancer, Harrison's Principles of Internal Medicine*, 13th ed., Isselbacher et al., eds., McGraw-Hill, New York (1994), pages 1853–1858; *American Cancer Society Statistics, Cancer J. Clinicians*, 45:30 (1995). Epithelial ovarian cancer, the most common ovarian cancer, has a distinctive pattern of spread: cancer cells may migrate through the peritoneum to produce multiple metastatic nodules in the visceral and parietal peritoneum and the hemidiaphragms. In addition cancer cells metastasize through the lymphatic and blood vessels to areas such as the liver, lung and brain. Early stage ovarian cancer is often asymptomatic and is detected coincidentally by palpating an ovarian mass on pelvic examination. In pre-menopausal patients, about 95% of these masses are benign. Even after menopause, 70% of masses are benign but detection of any enlargement requires exploratory surgery. In postmenopausal women with a pelvic mass, a markedly elevated serum CA-125 level of greater than 65 U/ml indicates malignancy with a 96% positive predictive value. Chapter 321, *Ovarian Cancer, Harrison's Principles of Internal Medicine*, supra.

Epithelial ovarian cancer is seldom encountered in women less than 35 years of age. Its incidence increases sharply with advancing age and peaks at ages 75 to 80, with the median age being 60 years. The single most important risk factor for this cancer is a strong family history of breast or ovarian cancer. In families in which ovarian, breast, endometrial or colon cancer can be tracked as an apparent autosomal dominant trait, the risk of this cancer can be as high as 50%. Having a single first-degree relative with ovarian cancer increases a woman's risk by at least three-fold, and having a personal history of breast or colorectal cancer increases the risk of subsequently developing ovarian cancer by two-fold. Chapter 321, *Ovarian Cancer, Harrison's Principles of Internal Medicine*, supra. In addition, those with identifiable genetic mutations in genes such as BRCA1 also have an increased risk. Baker et al., *Etiology, Biology, and Epidemiology of Ovarian Cancer, Seminars in Surgical Oncology* 10: 242–248, 1994; Amus et al., *Genetic Epidemiology of Epithelial Ovarian Cancer, Cancer* 71: 566–72, 1993; Whitmore, *Characteristics Relating To Ovarian Cancer Risk: Implications for Preventing and Detection, Gynecologie Oncology* 55, 515–19, 1994. Oncogenes associated with ovarian cancers include the HER-2/neu (c-erbB-2) gene, which is overexpressed in a third of ovarian cancers, the fms oncogene, and abnormalities in the p53 gene, which are seen in about half of ovarian cancers. A number of environmental factors have also been associated with a higher risk of epithelial ovarian cancer, including a high fat diet and intake of lactose in subjects with relatively low tissue levels of galactose-1-phosphate uridyl transferase.

Previously, there has existed no established pharmaceutical approach to the prevention of ovarian cancer. For all women, especially those at high risk of developing this disease, the only available option has been surgical removal of the ovaries, with all of the attendant risks and subsequent adverse health consequences due to resulting estrogen deficiency.

Of interest to the present invention is the disclosure of co-owned and copending U.S. patent application Ser. No. 08/713,834 filed Sep. 13, 1996 entitled "Prevention of Ovarian Cancer by Administration of Progestin Products" the disclosure of which is hereby incorporated by reference. This application discloses a method for preventing the development of epithelial ovarian cancer by administering progestin products, either alone or in combination with other agents, such as estrogen products. Specifically, a method is described for preventing ovarian cancer comprising administering to a female subject an amount of progestin product effective to increase apoptosis in ovarian epithelial cells of the female subject. Apoptosis is one of the most important mechanisms used for the elimination of cells that have sustained DNA damage and which are thus prone to transformation into malignant neoplasms. Thus, increasing apoptosis of ovarial epithelial cells will prevent the transformation of non-neoplastic, including normal and dysplastic, cells into neoplastic cells.

Vitamin D is a fat soluble vitamin which is essential as a positive regulator of calcium homeostasis. In the skin 7-Dehydrocholesterol (pro-Vitamin $D_3$) is photolyzed by ultraviolet light to pre-Vitamin $D_3$, which spontaneously isomerizes to Vitamin $D_3$. Vitamin $D_3$ (cholecalciferol), the structure of which is set out below, is converted into an active hormone by hydroxylation reactions occurring in the liver to produce 25-hydroxyvitamin $D_3$ which is then converted in the kidneys to produce 1,25-dihydroxyvitamin $D_3$ (1,25-dihydroxycholecalciferol, calcitriol, 1,25$(OH)_2D_3$) which is transported via the blood to its classic target organs, namely, the intestine, kidney, and bones. Vitamin $D_3$ and 1,25-dihydroxy vitamin $D_3$ are shown below:

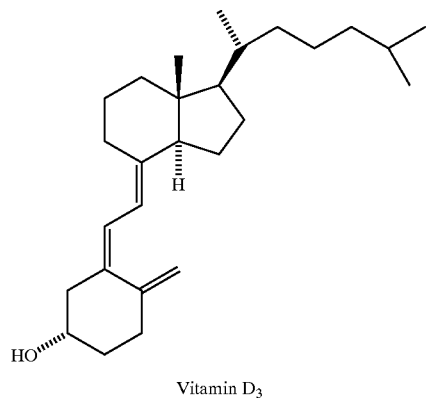

Vitamin $D_3$

-continued

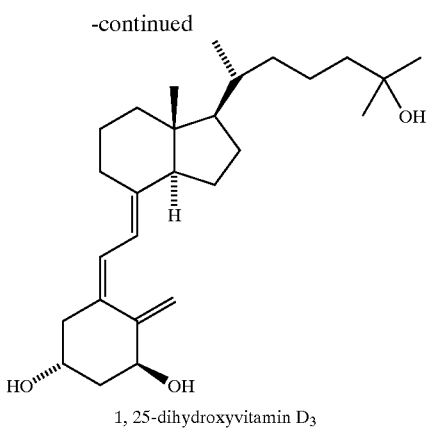

1, 25-dihydroxyvitamin $D_3$

Vitamin D deficiency in childhood produces rickets, which is characterized by inadequate calcification of cartilage and bone. In adults, Vitamin D deficiency leads to softening and weakening of bones, known as osteomalacia. The major therapeutic uses of Vitamin D are divided into four categories: (1) prophylaxis and cure of nutritional rickets, (2) treatment of metabolic rickets and osteomalacia, particularly in the setting of chronic renal failure, (3) treatment of hypoparathyroidism, and (4) prevention and treatment of osteoporosis. Recommended daily dietary allowances of Vitamin D by the Food and Nutrition Board of the United states National Research Council (1989) were 10 mg cholecalciferol (400 IU Vitamin D) daily for females age 11–24 and 5 mg cholecalciferol (200 IU Vitamin D) daily for females age 25 and older. Normal serum levels of 25-hydroxyvitamin $D_3$ are not closely regulated and it has a biological half-life of several weeks with blood levels typically ranging from 15 to 80 ng/mL. Serum levels of 1,25-dihydroxyvitamin $D_3$ are more closely regulated and typically range from 15–60 pg/mL. Serum 1,25-dihydroxyvitamin $D_3$ has a half-life of 6–8 hours. 1,25-dihydroxyvitamin $D_3$ partitions into cells by virtue of its lipophilicity, binds to intracellular receptors, and translocates to the nucleus where the complex controls the transcription of a number of genes, many of which relate to calcium metabolism. Corder et al., *Cancer Epidemiology, Biomarkers & Prevention* 2:467–472 (1993).

Certain compounds are known to upregulate the functional human Vitamin D receptor ("VDR"). For example, Santiso-Mere et al., *Molecular Endocrinology* Vol. 7, No. 7, pp.833–839 (1993) teach the expression of functional human vitamin D receptor (VDR) in *Saccharomyces cerevisiae*. This reference further teaches up-regulation of the VDR by 1,25-dihydroxyvitamin $D_3$. Davoodi et al., *J. Steroid Biochem. Molec. Biol.* 54: No. 3/4, pp. 147–153 (1995) relates to the effect of 1,25-dihydroxyvitamin $D_3$ on upregulation of the VDR. Davoodi et al. teach that progestins and transretinoic acid may also upregulate the VDR. Davoodi et al., at pp. 149–50.

Vitamin D and its analogues and derivatives are taught to have possible utility in the treatment, rather than prevention, of cancers by retarding tumor growth and in stimulating the differentiation of malignant cells to normal cells. For example, 1,25-dihydroxyvitamin $D_3$ possesses potent antileukemic activity by virtue of inducing the differentiation of leukemia cells to non-malignant macrophages.

Colston et al., *Endocrinology* Vol. 108, No. 3, 1083–1086 (1981) may have been the first to report antitumor effects of Vitamin D. This study reported the presence of specific, high-affinity receptors for 1,25-dihydroxy-vitamin $D_3$ in malignant melanoma and that in vitro administration of 1,25-dihydroxy-vitamin $D_3$ produced a marked increase in cell doubling time. Sato et al., *Tohoku J. exp. Med.* 138:445–446 (1982) reported the utility of 1a-Hydroxyvitamin $D_3$ in in vivo experiments relating to treatment of Sarcoma 180 and Lewis lung carcinoma implanted into mice. In these experiments the Vitamin D suppressed tumor growth or inhibited pulmonary metastases. Disman et al., *Cancer Research* 47: 21–25 (1987) disclose the utility of 1,25-dihydroxyvitamin $D_3$ in inhibiting the growth of human colonic cancer xenografts in mice. Dokoh et al., *Cancer Research* 44: 2103–2109 (1984) disclose the utility of 1,25-dihydroxyvitamin $D_3$ on cultured osteogenic sarcoma cells. The utility of 1,25-dihydroxyvitamin $D_3$ for inducing differentiation of leukemic cells is also known. See Mangelsdorf et al., *J. Cell Biol.* Vol. 98, 391–398 (1984).

Chida et al., *Cancer Research* 45: 5426–5430 (1985) describe the inhibition of the promotional phase of 7,12-dimethylbenz[a]anthracene-induced skin carcinogenesis in mice by 1,25-dihydroxyvitamin $D_3$. Oikawa et al., *Anti-Cancer Drugs* 2: 475–480 (1991) disclose the antitumor effect of 22-oxa-1a,25-dihydroxyvitamin $D_3$ on rat mammary tumors induced by 7,12-dimethylbenz[a]anthracene.

Vitamin D and its metabolic products while potentially useful in retarding tumor growth have the disadvantage that they are very potent calcemic agents that cause elevated blood calcium levels by stimulating intestinal calcium absorption and bone calcium resorption. Accordingly, there has been a desire in the art for Vitamin D analogues and derivatives having variant activities such that, for example, antileukemic activity is enhanced without concomitant enhancement of calcemic activity. Frampton et al., *Cancer Research* 43: 4443–4447 (1983) disclose the inhibition of human breast cancer cell growth in vitro. The vitamin $D_3$ metabolites 1,24,25-$(OH)_3D_3$ and 1,25,26-$(OH)_3D_3$ were identified as analogues which would be effective in inhibiting tumor cell growth without exhibiting unacceptable bone resorption and hypercalcemia. Sporn et al., *Proc. Am. Assn. Cancer Res.* No. 34 Abstracts p. 622 (March 1993) report the utility of the vitamin D analogue 1,25-dihydroxy-16-ene-23-yne-26, 27-hexafluorocholecalciferol having greater potency than 1,25-dihydroxycholecalciferol in differentiating HL-60 leukemic cells but which is less active in its hypercalcemic effects.

There also exists a large patent literature relating to the use of Vitamin D analogues for retarding tumor growth and treatment of leukemias. Partridge et al., U.S. Pat. No. 4,594,340 teaches the syntheses of the Vitamin D analogues 25,26-dehydro-1a,24R-dihydroxycholecalciferol and 25,26-dehydro-1a,24S-dihydroxycholecalciferol as differentiation inducing agents and anti-proliferation agents useful in treating osteoporosis, tumors and leukemia. DeLuca et al., U.S. Pat. No. 4,800,198 discloses the use of secosterol compounds sharing structural similarity with Vitamin D for inducing differentiation of malignant cells in methods of treatment of leukemic disorders.

Binderup et al., U.S. Pat. No. 5,190,935 disclose Vitamin D analogues having antiproliferative effects on cancer cells. Calverly et al., U.S. Pat. No. 5,206,229 disclose Vitamin D analogues exhibiting antiinflammatory and immunomodulating effects which also exhibit strong activity in inducing differentiation and inhibiting undesirable proliferation of certain cells. DeLuca et al., U.S. Pat. No. 5,246,925 disclose 1a-hydroxy-19-nor-vitamin D analogues which exhibit activity in arresting the proliferation of undifferentiated cells, including malignant cells, and in inducing their differentiation. Ikekawa et al., U.S. Pat. No. 5,278,155 disclose Fluorine-containing vitamin $D_3$ analogues which showed in vitro activity in inducing differentiation of human colonic cancer cells. DeLuca et al., U.S. Pat. No. 5,373,004 disclose 26,28-methylene-1a,25-dihydroxyvitamin $D_2$ compounds having unique preferential calcemic activity. Calverley et al., U.S. Pat. No. 5,374,629 disclose Vitamin D analogues having antiinflammatory and immunomodulating effects as well as strong activity in inducing differentiation and inhibiting proliferation of cancer cells. DeLuca et al., U.S. Pat. No. 5,380,720 disclose 1a-hydroxy-22-iodinated vitamin $D_3$ compounds capable of inducing relatively high differentiation of s malignant cells. Hansen et al., U.S. Pat. No. 5,387,582 disclose Vitamin D analogues having activity in inducing differentiation of cancer cells and skin cells. Posner et al., U.S. Pat. No. 5,389,622 disclose a Vitamin $D_3$ analogue having growth inhibition activities against murine kerotinocyte cells. Calverley et al., U.S. Pat. No. 5,401,731 disclose Vitamin D analogues having activity in the prophylaxis of autoimmune diseases.

Neef et al., U.S. Pat. No. 5,411,949 disclose 23-Oxa-derivatives of Vitamin D having proliferation inhibiting and cell-differentiation effects. Doran et al., U.S. Pat. No. 5,428,029 disclose Vitamin $D_3$ fluorinated analogues as agents for the treatment of tumors such as breast cancer, as agents for the treatment of neoplastic diseases such as leukemia, and as agents for the treatment of sebaceous gland diseases. Neef et al., U.S. Pat. No. 5,446,035 disclose 20-methyl-substituted Vitamin D derivatives exhibiting improved induction of cell differentiation as compared to calcitriol in an HL-60 cell line. Baggiolini et al., U.S. Pat. No. 5,451,574 and U.S. Pat. No. 5,512,554 disclose Vitamin $D_3$ fluoridated analogues as agents for treatment of cancer, such as leukemia and or hyperproliferative skin diseases such as psoriasis. DeLuca et al., U.S. Pat. No. 5,484,782 disclose (E)-20(22)-dehydrovitamin D compounds having relatively high HL-60 cell differentiation activity. Neef et al., U.S. Pat. No. 5,532,228 disclose Vitamin D derivatives having cell proliferation-inhibiting and cell-differentiating activity. DeLuca et al., U.S. Pat. No. 5,536,713 disclose 19-nor-Vitamin $D_3$ compounds with substituents at the 2-position which exhibit activity in inducing differentiation of malignant cells with little or no bone calcification activity. Dore et al., U.S. Pat. No. 5,547,947 disclose methods of inducing inhibition or loss of cell proliferation in solid tumors utilizing a Vitamin $D_3$ analogue alone or in combination with a trans retinoic acid. Grue-Sorensen et al., U.S. Pat. No. 5,554,599 disclose 22-thio Vitamin D derivatives exhibiting antiinflammatory and immunomodulating effects which also exhibit strong activity in inducing differentiation and inhibiting undesirable proliferation of certain cells.

The use of 1,25-dihydroxyvitamin $D_3$ for treatment of gynecologic neoplasms including ovarian carcinomas is proposed in various references, but its efficacy against ovarian cancer cells is unclear. Moreover, there is no suggestion that Vitamin D will inhibit conversion of non-neoplastic ovarian cells to neoplastic ovarian cells or will promote apoptosis in non-neoplastic ovarian cells. Specifically, Christopherson et al., *Am. J. Obstet Gynecol.* Vol 155, No. 6. 1293–1296 (1986) report that 1,25-dihydroxhcholecalciferol is useful in inhibiting the replication of various malignant human cells but that administration of 1,25-dihydroxhcholecalciferol in ovarian adenocarcinoma cells was associated with an increase in the rate of cancer cell growth when treated at a concentration of 10 nmol/L. In contrast, Saunders et al., *Gynecologic Oncology* 44: 131–136 (1992); and Saunders et al., *Gynecologic Oncology* 51: 155–159 (1993) report the in vitro inhibition of endometrial carcinoma cell growth by the combination of 1,25-dihydroxyvitamin $D_3$ with the antineoplastic agent carboplatin; and Saunders et al., *AntiCancer Drugs* 6 562–569 (1995) report inhibition of growth in breast and ovarian carcinoma cells by 1,25-dihydroxyvitamin $D_3$, when combined with retinoic acid and dexamethasone. Thus, based on the results of these studies, it is unclear whether Vitamin D is itself useful for the inhibition of ovarian cancer cell growth. More significantly, none of these studies describe the effect, or suggest any effect, of Vitamin D on growth or apoptosis of non-neoplastic ovarian epithelial cells.

Similarly, while references suggest that Vitamin D may be effective to induce apoptosis in breast cancer cells, those references do not suggest that Vitamin D may effect the growth or apoptosis of non-neoplastic breast cells. For example, Welsh, *Biochem. Cell Biol.* 72: 537–545 (1994) discloses the in vitro use of 1,25-dihydroxyvitamin $D_3$ in combination with the antiestrogen 4-hydroxytamoxifen to induce apoptosis in the breast cancer cell line MCF-7. However, Welsh makes no suggestion that Vitamin $D_3$ can induce apoptosis in normal or non-malignant cells.

The teachings of Narvaez et al., *Endocrinology* Vol. 137, No. 2 pp 400–409 (1996) are in accord with the references discussed above. Narvaez et al. teach (1) that Vitamin D can have effects on malignant cells, but the effects are cell type specific and unpredictable and (2) that, to the extent tested, Vitamin D did not have any effect on non-malignant cells. Specifically, Narvaez et al., teach that 1,25-dihydroxyvitamin $D_3$ is a negative growth regulator of breast cancer epithelial cells and that its effects are mediated via the nuclear vitamin D receptor (VDR). The reference also suggests that the reduction in the in vitro growth of the MCF-7 breast cancer cell line in response to 1,25-dihydroxyvitamin $D_3$ is associated with morphological and biochemical evidence of cancer cell death by apoptosis. Narvaez et al. disclose selection of a variant line of MCF-7 cells resistant to the growth inhibitory effects of 1,25-(OH)$_2D_3$. The MCF-7$^{D3Res}$ cells express the VDR but are resistant to induction of apoptosis in response to 1,25-(OH)$_2D_3$ and structurally related compounds. Despite vitamin $D_3$ resistance, the MCF-7$^{D3Res}$ cells are sensitive to induction of apoptosis in response to antiestrogens.

Narvaez et al. further teach that Vitamin D had no apoptotic effect on the normal cells which they studied. Specifically, the reference teaches that doses of the vitamin D analog EB 1089 which cause breast tumor regression in rats have no growth or apoptotic effects in vivo on normal intestine and kidney cells of rats treated with the analog. Narvaez et al. further investigated the possibility that 1,25-dihydroxyvitamin $D_3$ might be able to induce apoptosis in cell lines of normal tissues such as intestinal crypt cells and normal renal epithelial cells which express high levels of the VDR and known vitamin $D_3$-regulated proteins. Although the 1,25-dihydroxy vitamin $D_3$ induced vitamin D dependent proteins in both cell lines, no evidence of apoptosis was observed even when the cells were treated with 500 nM 1,25-dihydroxy vitamin $D_3$. In addition, no inhibitory effects on growth nor induction of apoptosis were observed in the intestine or kidney cells of rats treated with a vitamin D analogue (EB 1089) in doses previously shown to cause breast tumor regression.

Narvaez et al. state that these and other data "suggest that although a functional VDR may be necessary for the growth regulatory effects of 1,25-(OH)$_2D_3$, its activation is not sufficient for triggering these effects. Thus, we hypothesize that induction of apoptosis by the 1,25-$(OH)_2D_3$-VDR complex is cell type specific." Accordingly, although the effects of Vitamin D are mediated by the VDR, the expression of the receptor by cells does not determine how they will respond to Vitamin D. For example, Vitamin D has potent effects on kidney cells and intestinal cells relating to calcium homeostasis, but does not cause apoptosis. On the other hand, Vitamin D might inhibit the growth of certain malignant cell lines or cause apoptosis of such cell lines. The only specific cell types for which Narvaez et al. were able to establish apoptosis through administration of Vitamin D were certain malignant cells. Narvaez et al. observed no apoptotic effect on any non-malignant cells studied. Accordingly, although ovarian epithelial cells express the VDR it would not have been expected by those skilled in the art that Vitamin D would have apoptotic effects on normal ovarian epithelial cells.

Also of interest to the present invention is the epidemiologic study of Lefkowitz et al., *International Journal of Epidemiology* vol 23, No. 6 pp 1133–1136 (1994) reporting that sunlight exposure may reduce the risk of ovarian cancer mortality. Using population based data regarding ovarian cancer mortality in large cities across the United States, as well as geographically based long-term sunlight data reported by the National Oceanic and Atmospheric Administration, the authors found an inverse correlation between regional sunlight exposure and ovarian cancer mortality risk. The publication refers to the antineoplastic effect of vitamin D against cancer lines and tumors as demonstrated in in vivo and in vitro studies and suggests that this antineoplastic effect may be reducing the ovarian cancer mortality rates for the regions with more sunlight. Thus, this study teaches that Vitamin D may have an effect on malignant cells. There is no teaching or suggestion that sunlight may have any effect on non-neoplastic cells or that the protective effect of sunlight may be mediated by an effect of enhanced levels of Vitamin D on non-neoplastic ovarian epithelial cells in vivo.

Studzinski et al., *Cancer Research* 55:4012–4022 (1995) also discuss the potential effect of Vitamin D from sunlight on retarding neoplastic progression of various cancers. Studzinski et al. refer to evidence that Vitamin D retards growth of cancer cells in vivo and in vitro, induces differentiation of cancer cells, and induces apoptosis in cancer cells, and that these effects may prevent cancer progression. Studzinski et al. do not suggest or imply that Vitamin D may have a preventative benefit through effect on non-malignant cells.

Thus, while the art reports various therapeutic activities of Vitamin D and its analogues and derivatives in retarding tumor growth, the effect of Vitamin D on ovarian carcinoma cells is unclear. Moreover there exists no suggestion that Vitamin D has activity in causing apoptosis in non-neoplastic cells or in inhibiting the conversion of non-neoplastic cells to neoplastic cells in any manner. Accordingly, there remains a need in the art for methods and compositions which will prevent cancers such as ovarian epithelial cancer by inhibiting the conversion of normal and dysplastic ovarian epithelial cells to neoplastic cells.

SUMMARY OF THE INVENTION

The present invention provides a method for preventing the development of epithelial ovarian cancer by administering an effective amount of Vitamin D compounds including Vitamin D and biologically active analogues and derivatives thereof to a female subject.

While the inventors do not wish to be bound by any particular theory, the present invention is based on the discovery that administration of Vitamin D compounds results in an accelerated rate of apoptosis in vitro in non-neoplastic human ovarian epithelial cells including benign and dysplastic ovarian epithelial cells. Apoptosis is one of the most important mechanisms used for the elimination of cells that have sustained DNA damage and which are thus prone to transformation into malignant neoplasms. By augmenting the apoptosis pathway, Vitamin D compounds including Vitamin D and biologically active analogues and derivatives thereof may thus enhance the efficient removal of pre-neoplastic ovarian epithelial cells, thereby decreasing the risk of developing epithelial ovarian carcinoma.

Thus, the invention provides methods of inhibiting conversion of non-neoplastic ovarian epithelial cells to neoplastic cells comprising administering to a female subject an amount of Vitamin D or a biologically active analogue or derivative thereof effective to increase apoptosis in non-neoplastic ovarian epithelial cells of a female subject. The invention further provides methods of increasing apoptosis of non-neoplastic ovarian epithelial cells of a female subject comprising administering to a female subject an amount of Vitamin D or a biologically active analogue or derivative thereof effective to increase apoptosis in ovarian epithelial cells of the subject.

DETAILED DESCRIPTION OF THE INVENTION

The present invention generally relates to methods for preventing the development of epithelial ovarian cancer by administering Vitamin D compounds in an amount effective to increase apoptosis of ovarian epithelial cells. The invention also provides a method of increasing apoptosis in ovarian epithelial cells of a female subject comprising administering to a female subject an amount of a Vitamin D compound including Vitamin D or an analogue or derivative thereof effective to increase apoptosis in ovarian epithelial cells of the female subject.

The present invention is related to the discovery that administration of 1,25-dihydroxyvitamin $D_3$ and 24,25-dihydroxyvitamin $D_3$ each induced an accelerated rate of apoptosis in vitro in human ovarian epithelial cells. Apoptosis is a process whereby a genetic program within the cell is activated to trigger a specific series of events within the cell eventually leading to the death and efficient disposal of the cell. Richard Lockshin, Zahra Zakeri, *The Biology of Cell Death and Its Relationship to Aging in Cellular Aging and Cell Death*, pp. 167–180, 1996. Wiley-Liss Inc., Editors: N.J. Holbrook, G. Martin, R. Lockshin. C. Miligan, L. Schwartz, *Programmed Cell Death During Development of Animals in Cellular Aging and Cell Death*, pp. 181–208, 1996. Wiley-Liss Inc. P53-*Dependent Apoptosis in Tumor Progression and in Cancer Therapy*, Scott W. Lowe, H. Earl Ruley in *Cellular Aging and Cell Death*, pp. 209–234, 1996. Wiley-Liss, Inc.

For cells that have sustained DNA damage, apoptosis is one of the most important mechanisms used for the elimination of these cells, the preservation of which could otherwise lead to the development of malignant neoplasms. Canman et al., DNA *Damage Responses: P-53 Induction, Cell Cycle Pertubations, and Apoptosis*, Cold Spring Harbor Symp. Ouant. Biol., 59:277–286 (1994). Thus, the apoptosis pathway is a virtually universal safeguard to prevent the persistence and proliferation of damaged cells that can be lethal to the organism. For normal tissues, the processes of cell proliferation and cell death are usually in a steady-state balance, and the apoptosis mechanism not only serves to prevent overgrowth of tissue, but also to eliminate those cells that are aberrant and therefore prone to resist normal growth regulatory controls.

An accelerated rate of apoptosis would facilitate the destruction and thereby removal of ovarian surface epithelial cells which have defective DNA and which have the potential to transform into malignant neoplasms. Given the importance of the apoptotic pathway for removal of abnormal cells from tissues, and thus the protection of normal tissues from neoplastic transformation, it is possible that the induction of apoptosis by Vitamin D is one mechanism underlying the effect of exposure to sunlight in reducing the risk of ovarian cancer.

The term "Vitamin D compound" including "Vitamin D" "Vitamin D analogue" or "Vitamin D derivative" as used herein includes any compound which activates the Vitamin D Receptor, by binding or otherwise, either in its form of administration or in a form to which it is converted by processing by the human body. This definition thus includes each of Vitamins $D_1$, $D_2$, $D_3$, $D_4$ and $D_5$ and the various known analogues and derivatives thereof and any other agent that has Vitamin D activity or is an agonist thereof and that thereby increases the rate of apoptosis in ovarian epithelial cells. It is contemplated that not only presently available Vitamin D analogues and derivatives but also Vitamin D analogues and derivatives introduced in the future will be useful according to the present invention. Given the ability to produce the VDR recombinantly as described by Santiso-Mere et al., supra and models for determining VDR activation efficiency those of ordinary skill would be capable of identifying suitable Vitamin D compounds useful for practice of the present invention. Suitable analogues and derivatives are expected to include but are not limited to the following: 1α-hydroxyvitamin $D_3$; 25-hydroxyvitamin $D_3$; 1,24,25-(OH)$_3D_3$; 24,25-(OH)$_2D_3$; 1,25,26-(OH)$_3D_3$; 24,25-(OH)$_2D_3$; 1,25-dihydroxy-16-ene-23-yne-26, 27-hexafluorocholecalciferol; 25,26-dehydro-1a, 24R-dihydroxycholecalciferol and 25,26-dehydro-1a,24S-dihydroxycholecalciferol; 1a-hydroxy-19-nor-vitamin D analogues; 26,28-methylene-1a,25-dihydroxyvitamin $D_2$ compounds; 1a-hydroxy-22-iodinated vitamin $D_3$ compounds; 23-Oxa-derivatives of Vitamin D; and fluorinated Vitamin D analogues; 20-methyl-substituted Vitamin D derivatives; (E)-20(22)-Dehydrovitamin D compounds; 19-nor-Vitamin $D_3$ compounds with substituents at the 2-position; and 22-thio Vitamin D derivatives.

Appropriate dosages to increase the induction of apoptosis of non-neoplastic ovarian epithelial cells may be determined by those of skill in the art depending upon the identity of the Vitamin D compound and its method of administration. For example, preferred dosages of the Vitamin D compound effective to increase apoptosis of non-neoplastic ovarial epithelial cells range from 0.0001 to 1.0 mg/kg of body weight (based upon the apoptotic potency of 1,25-dihydroxyvitamin $D_3$) with dosages ranging from about 0.005 to 0.75 mg/kg being more preferred and dosages of about 0.05 to 0.5 mg/kg being particularly preferred. It is hypothesized that even higher dosages of 1,25-dihydroxyvitamin $D_3$ may be more effective in inducing apoptosis. A Vitamin D analogue that has greater potency than 1,25-dihydroxyvitamin $D_3$ in inducing apoptosis and/or which does not have the deleterious side effects of 1,25-dihydroxyvitamin $D_3$, such as hypercalcemia, could be administered at a dosage equivalent much higher than 1.0 mg/kg of 1,25-dihydroxyvitamin $D_3$. While the potency and bioavailability of other Vitamin D compounds and I analogues may vary, those of skill in the art can determine their apoptotic potency in relation to 1,25-dihydroxyvitamin $D_3$ and appropriate dosages and regimens of administration through use of in vitro testing methods such as disclosed in the accompanying example.

Prophylactic regimens for administration of Vitamin D compounds for normal female individuals and for those at increased risk of ovarian epithelial cancer can include daily or other periodic administration of Vitamin D compounds. It is contemplated that preferred regimens for prevention of ovarian cancer may comprise periodic administration of relatively larger dosages of Vitamin D compounds on a monthly or less than monthly basis rather than more frequent administration. The larger dosage would preferably range from a dosage equivalent to at least 400 I.U., more preferably a dosage equivalent to at least 2000 I.U., or still more preferably a dosage equivalent to 4000 I.U. According to such a regimen, a larger dosage of a Vitamin D compound might induce apoptosis in a large cohort of normal or dysplastic epithelial cells which over a period of time have become available for apoptosis. The treatment is then repeated some time later when another cohort of epithelial cells is capable of being induced for apoptosis. It is contemplated that one mode of administration may be administering the Vitamin D compound for a brief period sufficient to produce apoptotic turnover of damaged ovarian cells, followed by repeated dosing periods at intervals, for example 1, 3, 6, or 9 months or 1, 3, 5, or 10 years, selected to provide apoptotic turnover adequate to prevent malignant transformations. The most preferable mode for administration would be one that maximizes the apoptotic turnover of ovarian epithelial cells and minimizes any side effects. The advantage of a technique of using large doses of Vitamin D on an infrequent basis is that it may minimize the adverse calcemic effects of a more frequent administration of Vitamin D compounds. The efficacy of such a technique is supported by the recognition that 1,25-dihydroxyvitamin $D_3$, the active metabolite of Vitamin D, has a relatively short serum half-life and that its apoptotic effect may be based on transient surges in serum levels. It is also possible that the apoptotic effect may not result entirely from the interaction of 1,25-dihydroxyvitamin $D_3$ (or its analogues) with the Vitamin D receptor but result from the effects of other Vitamin D compounds such as 25 hydroxyvitamin $D_3$ on the VDR. Furthermore, the inventors do not wish to be bound by the theory presented above for the efficacy of Vitamin D in preventing epithelial ovarian cancer. While it is believed that increased apoptosis is the responsible mechanism, it may be that other mechanisms are responsible.

In one mode of practicing this invention, it is first determined that a patient does not display any signs of ovarian cancer. The patient may in the alternative or addition be determined to be a female at high risk of developing ovarian cancer. A regimen of Vitamin D product, alone or in combination with other compounds, is then prescribed for the female patient.

As a further aspect of the invention it is contemplated that Vitamin D and analogues and derivatives thereof may be co-administered with other agents which promote apoptosis of non-neoplastic ovarian epithelial cells. One particularly preferred class of agents are the progestins as disclosed in co-owned and copending U.S. patent application Ser. No. 08/713,834 filed Sep. 13, 1996, the disclosure of which is incorporated herein by reference. According to one preferred aspect of the invention, Vitamin D compounds may be administered in combination with a progestin product in amounts which will induce apoptosis of non-neoplastic epithelial cells. It is contemplated that combinations of Vitamin D compounds and progestins will exhibit not only additive but synergistic effects in the induction of apoptosis of non-neoplastic ovarian epithelial cells. In this manner the adverse physiological effects of administering larger quantities of Vitamin D compounds and of progestin products can be minimized.

The term "progestin product" as used herein includes any drug which binds to the progestin receptor and induces a progestational effect. This definition thus includes all of the known progestins, derivatives of progesterone or testosterone that have progestin activity, and progestin agonists. It is contemplated that not only presently available progestins but also progestins introduced in the future will be useful according to the present invention. The known synthetic progestins are mainly derivatives of 17-alpha-hydroxy-progesterone or 19-nortestosterone. These progestins can be classified into three groups: the pregnane, estrane, and gonane derivatives. Progestin products may be administered at a variety of dosages including at a dose less than or equal to a dose equivalent to 10 mg daily of norethindrone, more preferably less than or equal to 1 mg daily, or less than or equal to 0.2 mg daily, and possibly as low as 0.05 mg daily of a norethindrone equivalent dose. According to a preferred aspect of the invention, a vitamin D compound and a progestin may be coadministered as a pharmaceutical composition preferably in a single unit dosage, such as a tablet, for inhibiting the conversion of non-neoplastic ovarian epithelial cells to neoplastic cells. The pharmaceutical composition comprises a Vitamin D compound and a progestin product in amounts which are together effective to increase apoptosis in non-neoplastic ovarian epithelial cells. Preferred pharmaceutical compositions include those wherein the Vitamin D compound is present at a dosage equivalent of from 0.0001 to 1.0 mg 1,25-dihydroxyvitamin $D_3$/kg of body weight and wherein the progestin product is present at a dosage less than, or equal to, a dosage equivalent to 10 mg of norethindrone or 1 mg of norethindrone. More preferred compositions comprise those wherein the Vitamin D compound is present at a dosage equivalent of from 0.005 to 0.1 mg 1,25-dihydroxyvitamin $D_3$/kg of body weight and wherein the progestin product is present at a dosage less than or equal to a dosage equivalent to 1 mg of norethindrone.

According to another dosage regimen a progestin product may be administered at a dose higher than 10 mg daily of a norethindrone equivalent dose. The oral preparations currently on the market are: norgestrel 0.075 mg, medroxyprogesterone acetate 2.5 mg, 5.0 mg, and 10.0 mg, norethindrone 0.35 mg, and norethindrone acetate 0.50 mg but it is contemplated that any of the progestins would be useful for combination with Vitamin D.

It is hypothesized that the combination of Vitamin D and progestins would have a synergistic effect, with reduced adverse side effects, based at least in part on the ability of the progestin compounds to upregulate the VDR. For that reason, it is contemplated in another aspect of the present invention that other compounds known to upregulate the VDR may be co-administered with the Vitamin D compounds. Such compounds include Vitamin A derivatives, such as retinoic acid, and also include dexamethasone.

Another aspect of the present invention involves the use of Vitamin D in combination with hormones at levels sufficient to provide the dual benefits of contraceptive protection and prevention of ovarian cancer. As discussed above, Vitamin D can be co-administered with progestins. Similarly, Vitamin D can be co-administered with estrogens and progestins at levels sufficient to provide contraceptive protection. The levels of estrogen and/or progestin for contraceptive protection are well known in the art. (See Speroff et al., *Clinical Gynecologic Endocrinology and Infertility* (Chap. 15), 4th Ed. 1989, incorporated herein by reference).

Yet another aspect of the present motion involves the co-administration of Vitamin D with hormones at levels sufficient for hormone replacement therapy. Estrogen is the primary agent in hormone replacement therapy. Postmenopausal women are generally given estrogen alone, or with low doses of progestins. The hormones may be administered continuously or cyclically. Continuous administration is typically 0.625 mg Premarin® (a conjugated equine estrogen) daily or its equivalent, with a 2.5 mg Provera® (medroxyprogesterone acetate) daily. Cyclical administration is typically 25 consecutive days of 0.625 mg Premarin® daily, with 10 mg Provera® daily on days 16 through 25, followed by 5 days of no hormone treatment (during which time these women will menstruate). (See Danforth's Obstetrics and Gynecology, Chapter 42, 7th Ed. 1994, incorporated herein by reference). Exemplary regimens according to this aspect of the present invention include doses of Vitamin D compounds with estrogen (with or without other compounds such as progestins) at levels sufficient for hormone replacement therapy.

Estrogen is believed to be possibly linked to ovarian cancer. For that reason, the combination of Vitamin D with estrogen would provide a pharmaceutical composition which would reduce the risk of developing ovarian cancer.

"Concurrent administration" or "co-administration" as used herein includes administration of the agents together, or before or after each other. The agents may be administered by different routes. For example, one agent may be administered intravenously while the second agent is administered intramuscularly, intravenously or orally. They may be administered simultaneously or sequentially, as long as they are given in a manner sufficient to allow both agents to achieve effective concentrations in the body. The preferred manner of co-administration for all the combinations described above is a single unit dosage, such as a single tablet.

All doses given herein are appropriate for a female subject of about 60 kg weight; the dosages naturally will vary more or less depending on the weight of the subject. The doses may be increased or decreased, and the duration of treatment may be shortened or lengthened as determined by the treating physician. The frequency of dosing will depend on the pharmacokinetics parameters of the agents and the route of administration. The optimal pharmaceutical formulation will be determined by one skilled in the art depending upon the route of administration and desired dosage. See for example, Remington's Pharmaceutical Sciences, 18th Ed. (1990, Mack Publishing Co., Easton, Pa. 18042) pages 1435–1712, the disclosure of which is hereby incorporated by reference. Such formulations may influence the physical state, stability, rate of in vivo release, and rate of in vivo clearance of the administered agents.

Those of ordinary skill in the art will readily optimize effective dosages and concurrent administration regimens as determined by good medical practice and the clinical condition of the individual patient. Regardless of the manner of administration, the specific dose may be calculated according to body weight, body surface area or organ size. Further refinement of the calculations necessary to determine the appropriate dosage for treatment involving each of the above mentioned formulations is routinely made by those of ordinary skill in the art and is within the ability of tasks routinely performed by them without undue experimentation, especially in light of the dosage information and assays disclosed herein. Appropriate dosages may be ascertained through use of established assays for determining dosages in conjunction with appropriate dose-response data. The final dosage regimen will be determined by the attending physician, considering various factors which modify the action of drugs, e.g. the drug's specific activity, the responsiveness of the subject, the age, condition, body weight, diet and sunlight exposure of the patient, the severity of any infection, time of administration and other clinical factors. Given the teachings herein those of ordinary skill would be able to determine appropriate dosage levels of Vitamin D compounds for inducing apoptosis of non-neoplastic ovarian epithelial cells.

It is contemplated that the routes of delivery of Vitamin D compounds including Vitamin D and biologically active analogues and derivatives thereof (either alone or in combination with other pharmaceuticals) could include oral, sublingual, injectable (including short-acting, depot, implant and pellet forms injected subcutaneously or intramuscularly), vaginal creams, suppositories, pessaries, rings, rectal suppositories, intrauterine devices, and transdermal forms such as patches and creams.

The term "females at high risk of developing ovarian cancer" includes females with a family history of breast or ovarian cancer, females with a prior history of breast or ovarian cancer, or females with a mutation in the BRCA1 gene or any other mutation shown to be associated with a high risk of developing ovarian cancer.

Other aspects and advantages of the present invention will be understood upon consideration of the following illustrative examples.

EXAMPLE 1

Example 1 addresses the effect of administration of Vitamin D on human ovarian epithelial cells. According to this example, a cell culture derived from normal ovarian epithelial cells was plated in 24 well plates at a concentration of 100,000 cells per well. After 24 hours, the wells were treated with 1,25-dihydroxyvitamin $D_3$ at a 100 nM concentration or control medium, and allowed to incubate for 96 hours. All experiments were carried out in triplicate. After 96 hours, cell lysates were extracted from each of the wells, and the cytoplasmic fraction was normalized for cell number and analyzed for DNA-histone complexes indicative of apoptosis using a cell death ELISA (Boehringer Mannheim). A significant (300%) increase in apoptosis (p=.01) was measured in the human ovarian epithelial cells treated with Vitamin D as compared with the controls.

EXAMPLE 2

A spontaneously transformed yet non-malignant epithelial cell culture derived from normal human ovarian epithelial cells was plated in pronectin coated 6-well dishes at a concentration of 250,000 cells per well. The cells were allowed to plate and then grow to 70% confluence. The wells were then washed, and the medium was replaced with phenol red free, dextran charcoal treated medium containing 2% fetal calf serum, and treated with 500 ng/ml of 24,25 $(OH)_2D_3$ for 72 hours. The cells were harvested, centrifuged, and the resultant cell pellets were resuspended in lysis buffer. DNA was precipitated using the Puregene DNA Isolation Kit (Gentra Systems, Minneapolis, Minn.). Equal amounts of DNA were then subjected to electrophoresis on a horizontal 1.5% agarose gel containing ethidium bromide and visualized under UV illumination. On electrophoresis, DNA laddering (the hallmark of apoptosis) was observed in cells treated with 24,25 Vitamin $D_3$, but not in the control, untreated cells.

While the above studies relate to non-neoplastic ovarian epithelial cells, it is further hypothesized that administration of Vitamin D can prevent breast cancer by causing apoptosis of non-neoplastic breast cells. Prevention of breast cancer could be achieved by administration of Vitamin D, alone or in combination with other agents and/or VDR upregulators, in an amount sufficient to cause apoptosis of non-neoplastic breast cells.

Numerous modifications and variations in the practice of the invention are expected to occur to those skilled in the art upon consideration of the foregoing description on the presently preferred embodiments thereof. Consequently the only limitations which should be placed upon the scope of the present invention are those that appear in the appended claims.

What is claimed is:

1. A method of reducing the risk of ovarian cancer in a female subject comprising administering to a female subject in need thereof an enhanced effective amount of a Vitamin D product sensitive to ovarian cancer risk reduction and a progestin product sensitive to ovarian cancer risk reduction wherein said progestin product and said Vitamin D product are provided in amounts effective to inhibit conversion of non-neoplastic ovarian epithelial cells of the female subject to neoplastic cells.

2. The method of claim 1 wherein the progestin product is administered at a dosage greater than or equal to a dosage equivalent to 10.0 mg of norethindrone.

3. The method of claim 1 wherein the progestin product is administered at a dosage greater than or equal to a dosage equivalent to 5.0 mg of norethindrone.

4. The method of claim 3 wherein the progestin product is levonorgestered.

5. The method of claim 3 wherein the Vitamin D compound is administered at a dosage of at least 2000 I.U.

6. The method of claim 1 wherein the progestin product is administered at a dosage less than or equal to a dosage equivalent to 1.0 mg of norethindrone.

7. The method of claim 1 wherein the progestin product is administered at a dosage less than or equal to a dosage equivalent to 0.2 mg of norethindrone.

8. The method of claim 1 wherein said progestin product is a gonane derivative.

9. The method of claim 1 wherein the female subject is at high risk of developing ovarian cancer reducing risk.

10. The method of claim 1 wherein said non-neoplastic cells are dysplastic cells.

11. The method of claim 1 wherein said progestin and said Vitamin D compound are administered in at least one single unit dosage.

12. The method of claim 1 wherein said Vitamin D product is 1,25-dihydroxyvitamin $D_3$, and said progestin product is levonorgestrel.

* * * * *